United States Patent
Lemole, Jr.

(10) Patent No.: US 8,518,041 B2
(45) Date of Patent: Aug. 27, 2013

(54) MODULUS PLATING SYSTEM

(75) Inventor: Michael G. Lemole, Jr., Burr Ridge, IL (US)

(73) Assignee: Lanx, Inc., Broomfield, CO (US)

( * ) Notice: Subject to any disclaimer, the term of this patent is extended or adjusted under 35 U.S.C. 154(b) by 232 days.

(21) Appl. No.: 12/766,728

(22) Filed: Apr. 23, 2010

(65) Prior Publication Data

US 2010/0211108 A1    Aug. 19, 2010

Related U.S. Application Data

(63) Continuation of application No. 10/405,132, filed on Apr. 1, 2003, now abandoned.

(60) Provisional application No. 60/369,245, filed on Apr. 1, 2002.

(51) Int. Cl.
*A61F 2/30*  (2006.01)

(52) U.S. Cl.
USPC ............................. 606/71; 606/250; 606/289

(58) Field of Classification Search
USPC ............... 623/17.11–17.16; 606/61, 71, 70, 606/280–299, 250–253
See application file for complete search history.

(56) References Cited

U.S. PATENT DOCUMENTS

| | | |
|---|---|---|
| 1,105,105 A | 7/1914 | Sherman |
| 3,680,553 A | 8/1972 | Seppo |
| 3,693,616 A | 9/1972 | Roaf et al. |
| 4,003,376 A | 1/1977 | McKay et al. |
| 4,905,679 A | 3/1990 | Morgan |
| 5,015,248 A | 5/1991 | Burstein et al. |
| 5,084,049 A | 1/1992 | Asher et al. |
| 5,108,395 A | 4/1992 | Laurain |
| 5,129,899 A | 7/1992 | Small et al. |
| 5,344,421 A | 9/1994 | Crook |
| 5,470,333 A | 11/1995 | Ray |
| 5,531,745 A | 7/1996 | Ray |
| 5,728,127 A | 3/1998 | Asher et al. |
| 5,741,261 A | 4/1998 | Moskovitz et al. |
| 6,001,130 A | 12/1999 | Bryan et al. |
| 6,152,927 A | 11/2000 | Farris et al. |
| 6,206,882 B1 | 3/2001 | Cohen |
| 6,214,004 B1 | 4/2001 | Coker |

(Continued)

FOREIGN PATENT DOCUMENTS

| | | |
|---|---|---|
| EP | 0455255 A1 | 11/1991 |
| WO | 00/64359 A1 | 11/2000 |

OTHER PUBLICATIONS

Askoxford.com definition of "I-beam.".
U.S. Appl. No. 09/560,415, filed Apr. 27, 2000.

*Primary Examiner* — Paul Prebilic
(74) *Attorney, Agent, or Firm* — Perkins Coie LLP

(57) ABSTRACT

In one embodiment, a modular system for cervical fixation is disclosed. The system comprises a first plate operable to be attached to a first vertebra and a second plate operable to be attached to a second vertebra. A fixation means for connecting the first v-plate to the second v-plate is provided. The fixation means can be any one of a number of devices including a pair of beams that connect to the first and second plate, an attachment plate that attaches the first and second plates and an attachment plate that has an elastic middle portion.

11 Claims, 8 Drawing Sheets

(56) References Cited

U.S. PATENT DOCUMENTS

| | | |
|---|---|---|
| 6,328,738 B1 | 12/2001 | Suddaby |
| 6,413,259 B1 | 7/2002 | Lyons et al. |
| 6,855,147 B2 | 2/2005 | Harrington, Jr. |
| 7,008,427 B2 | 3/2006 | Sevrain |
| 7,399,301 B2 | 7/2008 | Michelson |
| 8,048,076 B2 * | 11/2011 | Michelson ............ 606/71 |
| 2003/0036759 A1 | 2/2003 | Musso |
| 2005/0085816 A1 | 4/2005 | Michelson |
| 2005/0216010 A1 | 9/2005 | Michelson |
| 2010/0069968 A1 * | 3/2010 | Assaker et al. ............ 606/289 |

* cited by examiner though not limited to the description herein.

MODULUS PLATING SYSTEM

CROSS REFERENCE TO RELATED APPLICATIONS

This application is a continuation of U.S. Ser. No. 10/405,132 (now abandoned), which claims priority to U.S. Provisional Patent Application 60/369,245, filed on Apr. 1, 2002.

TECHNICAL FIELD OF THE INVENTION

This invention relates to medical devices and more specifically to a modulus plating system and method.

BACKGROUND OF THE INVENTION

Surgery for anterior cervical discectomy is performed with the patient lying on his or her back. A small incision is made in the front of the neck, to one side. After fat and muscle are pulled aside with a retractor, the disc is exposed between the vertebrae. An operating microscope may be used as part of the disc is removed with a forceps. Specialized instruments or a surgical drill may be used to enlarge the disc space. This will help the surgeon to empty the disc space fully and relieve any pressure on the nerve or spinal cord from bone spurs or the ruptured disc. If a bone graft is used, it will be placed in the disc space to help fuse the vertebrae it lies between. Any of several graft shapes may be used. In most cases, a cervical plate is applied to the cervical bodies surrounding the disc that was operated on. These cervical plates are one-piece plates that span one or more cervical bodies. An exemplary cervical plate is shown in FIG. 1. In the plate of FIG. 1, in use one end of cervical plate 1 is fixed to a vertebra and the other end of the cortical plate is attached to a second vertebra. One of the goals of a cervical plate is to improve initial stability in the postoperative period in order to decrease the need for wearing a cervical collar and result in a faster return to normal activities. In addition, anterior cervical plate fixation can potentially decrease the complications of graft dislocation, end plate fracture, and late kyphotic collapse. The operation is completed when the neck incision is closed in several layers. Unless dissolving suture material is used, the skin sutures (stitches) or staples will have to be removed after the incision has healed.

One of the drawbacks of current cervical plates and cervical plating system is that they are designed in one-piece units and may not always adaptable to cervical vertebra bodies of different sizes. Additionally, in certain designs, the bone screw that secures the plate to the cervical body can back out of the cervical body over time, loosening the cervical plates. Also, current cervical plates can only be applied at the end of surgery limiting their usefulness during the decompression and disc evacuation.

SUMMARY OF THE INVENTION

Thus a need has arisen for a modular plating system that overcomes a drawback of present cervical plating schemes. In the present invention, the cervical plate is a modular system consisting of at least two vertebra plates (v-plates) that attach to the vertebra body and a connecting plate that is mounted over and is attached to the v-plates.

In one embodiment, a modular system for cervical fixation is disclosed. The system comprises a first plate operable to be attached to a first vertebra and a second plate operable to be attached to a second vertebra. A fixation means for connecting the first v-plate to the second v-plate is provided. The fixation means can be any one of a number of devices including a pair of beams that connect to the first and second plate, an attachment plate that attaches the first and second plates and an attachment plate that has an elastic middle portion.

The present invention allows the use of one system to be used for any vertebral body size. Additionally, by mounting the v-plates early in the procedure, the v-plates can be used to anchor retractors and dissectors to aid in the discectomy procedure. Also, the attachment means for connecting plates are mounted over the v-plate, which helps to prevent the body screws of the v-plate from backing out. Additionally, a variable tension connector can be used to maintain tension between v-plates. A system for using talon shaped attachment means is also disclosed which provides benefits over current attachment means such as screws. A novel artificial disc system is disclosed, which provides for better disc replacement surgeries. Other technical benefits will be apparent from the description of the invention and appended claims.

BRIEF DESCRIPTION OF THE DRAWINGS

Non-limiting and non-exhaustive preferred embodiments of the present invention are described herein, with like numbers indicating like parts and where.

DETAILED DESCRIPTION OF THE DRAWINGS

This invention relates to components for use in a modulus plating system for cervical fixation. The system uses two or more v-plates, each of which is attached to a vertebra. After a surgical procedure is performed, the v-plates can be coupled in one of several ways to hold the vertebra together. However, the present invention is not limited solely to cervical fixation and can be applied to other spinal fixation system such as thoracic fixation, lumbar fixation, and possibly other applications such as appendicular skeleton applications and cranium applications. Thus, while the invention may be discussed primarily with regard to cervical fixation the inventive concepts are not limited to such.

Figure 2:
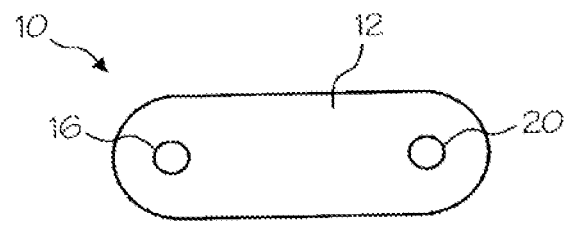
FIG. 2 is an illustration of a vertebral body plate (v-plate) in accordance with the teachings of the present invention.
Figure 1:
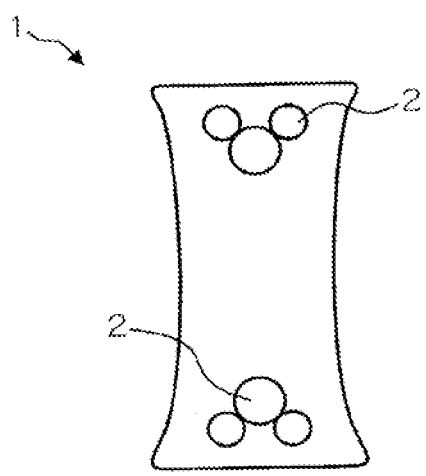
FIG. 1 is an illustration of a conventional vertebra plate.

FIG. 2 illustrates a vertebra body plate (v-plate) 10 in accordance with the teachings of the present invention. V-plate 10 is typically a one-piece plate that is generally oval in shape, although the exact shape and size of the v-plate 10 is unimportant as long as v-plate 10 can fit on to and secure on to a vertebra. V-plate 10 has a fixed thickness that depends on the choice of material and is chosen based on the strength needed to firmly attach it to the vertebra and support a fixation device in a system designed to connect to vertebra. V-plate 10 includes a body portion 12 having a first screw hole 16 and a second screw hole 20. Body screw 25, not pictured, is inserted through screw hole 16 and 20 to fix v-plate 10 to a vertebra and the like. While two screw holes are shown in FIG. 2, any number of screw holes may be used. Also, screw holes 16 and 20 can also be used as openings for bolts or other means to fix the v-plate to a bone.

V-plate 10 can be fabricated from a metal or metal alloy such as titanium or any other suitable material including radio-opaque carbon fiber constructs. The v-plate 10 can also be fabricated from a bio-absorbable material that can be absorbed back by the body. In a typical embodiment the v-plate 10 is approximately oval in shape and can be contoured such that the v-plate 10 will match the shape of the anterior vertebral body to which it is affixed. In one embodiment, bone screws (not pictured) are inserted into screw hole 16 and 20 to fix the v-plate 10 to the vertebral body. The screw holes may be fixed trajectory screw holes. Alternatively, any other fastening means known in the art can be used. V-plate 10 can also includes an interface (not pictured) for the fixation of an I-plate 50 or I-beams 30 as described in detail in FIGS. 5 through 9b. The use of a screw locking mechanism such as a locking washer or additional screws would typically not be necessary in the present invention because the I-plate 50 or I-beams 30 as described further in FIGS. 5 through 9b would at least partially cover the screws attaching the v-plate 10 to the vertebral body, thus preventing screw back out.

Figure 3:
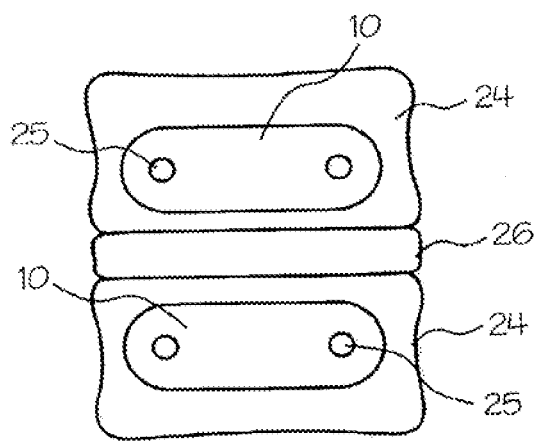
FIG. 3 is a drawing of a v-plate attached to a vertebra.

Two v-plates 10 are illustrated attached to two different cervical vertebra bodies 24 using body screws 25 in FIG. 3. Illustrated between the cervical vertebra bodies 24 is a disc 26. Unlike prior art vertebra plates, the v-plates 10 are installed prior to operating on the disc. The v-plates 10 can be used during surgery to help secure body structures.

Figure 4:
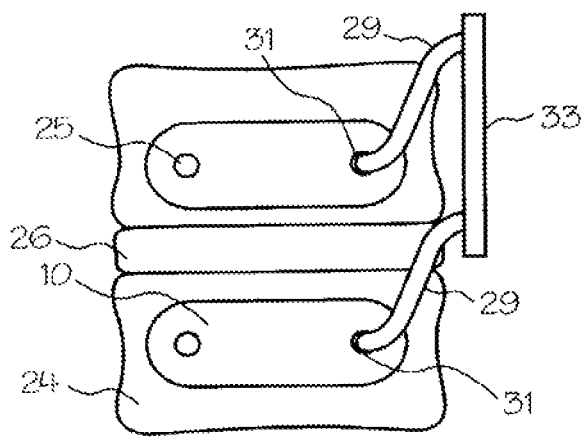
FIG. 4 is an illustration of the v-plate used to secure retractors and distractors.

FIG. 4 illustrates two v-plates 10 attached to vertebra bodies 24 on two discs 26. Retractor arms 29 can be attached to retractor arm anchor points 31 formed on the v-plate 10. The retractor arm anchor points 31 may be part of the screw holes of v-plate 10 or may be a separate structure on v-plate 10. Anchor points 31 can be any structure formed on v-plate that allows the retractor to be solidly mounted. The retractor arms 29 can be used during surgery to hold vital tissues such as the esophagus, the carotid artery and the trachea out of the way when the surgeon operates on the disc. This is advantageous because an additional person with manual retractors or a separate retractor system is not needed. Additionally, a ratcheting system 33 can be attached to the retractor arms 29. The ratcheting system 33 can be adjusting in a conventional manner in order to separate (distract) the cervical vertebra body for access to the disc 26. At the end of the procedure a fixation means is used to connect the two v-plates 10. While any structure that connects the two or more v-plates can be used as a fixation means, various embodiments of such fixation means are illustrated in FIG. 5 through FIG. 9b.

Figure 5:
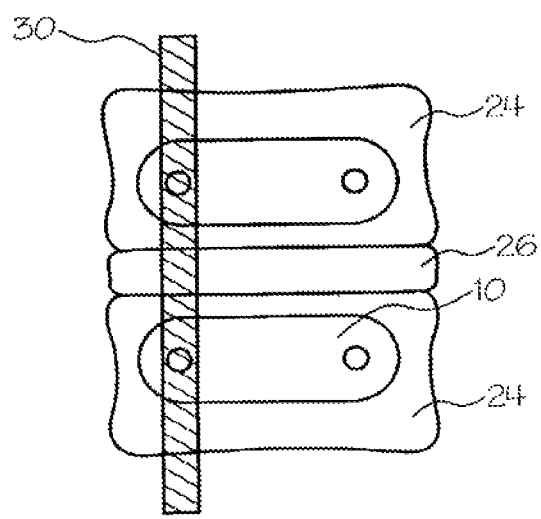
FIG. 5 is an embodiment of FIG. 3 with an I-beam attached to each v-plate.

FIG. 5 illustrates two v-plates 10 attached to cervical vertebra 24 with an I-beam fixing the v-plates 10. In a typical embodiment, two I-beams 30 are typically used to fix the v-plates 10 in place after graft is placed between vertebra bodies 24. In this illustration only one I-beam is shown attached to one side of v-plate 10 for simplification purpose, typically an I-beam is be placed on either side of v-plate 10 parallel to each other to enhance stability. I-beam 30 is generally a straight piece of metal such as titanium. I-beam 30 can be fastened directly on top of v-plates 10 using a screw or other fastening device. Typically, I-beam 30 will attach to v-plate 20 using a locking screw 40 or similar structures. I-beam 30 is designed to at least partially block the screws or other structure attaching the v-plate 10 to the vertebra body 24. This prevents the screws from baking out. Typically I-beam 30 is constructed of titanium or other rigid materials.

Figure 6:
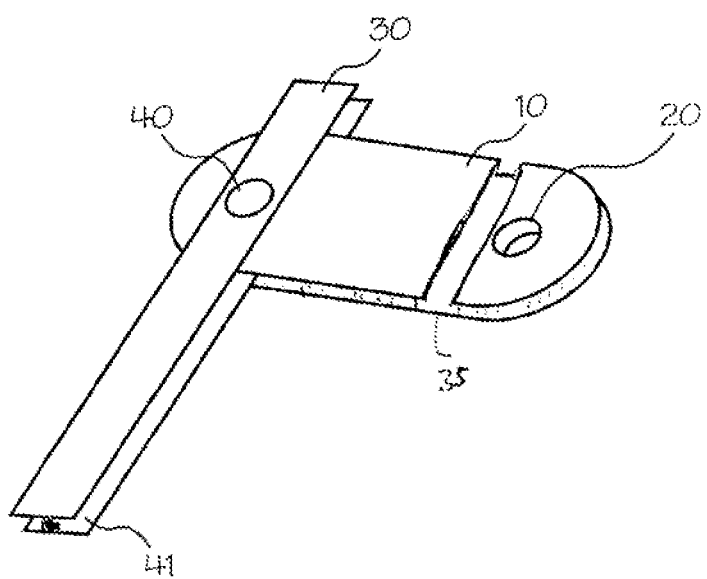
FIG. 6 is a detailed view of a modulus plate with an I-beam attached.

FIG. 6 illustrates the I-beam 30 as shown in FIG. 5 attached to a single v-plate 10 with a lock screw 40. In this embodiment I-beam 30 is inserted through a channel 35 formed on v-plate 10. A grove 41 of I-beam 30 is mated with the channel 35 and the I-beam 30 can be inserted through the channel 35. A locking screw or similar structure is then used to fix I-beam 30 to v-plate 10. Again, for simplicity, only one I-beam 30 is shown installed, typically I-beam 30 is installed in pairs with an I-beam 30 on either side of v-plate 10. Alternatively, the I-beam 30 could attach directly on top of v-plate 10, with the use of a locking screw 40.

Figure 7:
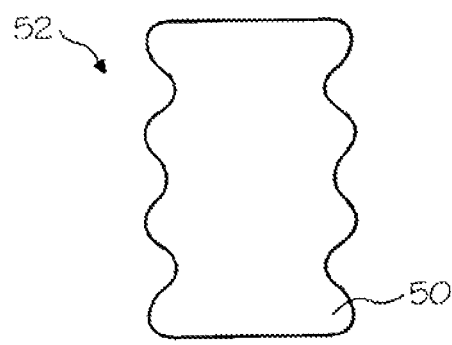
FIG. 7 is an illustration of an I-plate.
Figure 8:
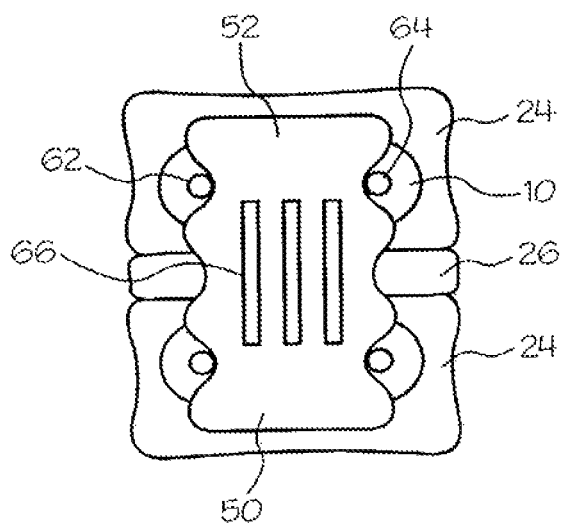
FIG. 8 is a drawing of an I-plate attached to two v-plates.

FIG. 7 illustrates a novel I-plate 50 for connecting v-plates 10 in accordance with the teachings of the present invention. I-plate 50 is a single structure designed to be mounted along the center of v-plate 10 as opposed to the I-beam 30, which is designed to be mounted along the side of v-plate 10. I-plate 50 can be constructed from titanium or any suitable material such as those used for v-plate 10. In one embodiment, I-plate 50 has a series of indentations 52 along each side for receiving a locking screw to help attach the I-plate to the v-plate 10 as seen in FIG. 8. In one embodiment, the radius of curvature of the indentations is greater than the radius of curvature of the screws or other structure used to attach the I-plate 50. This allows for the I-plate 50 to be angulated and adjusted to get the best fit between the I-plate 50 and v-plate 10. Two v-plates 10 along with I-plate 50 form the modulus plating system for a cervical level.

FIG. 8 illustrates I-plate 50 attached to two v-plates 10 which in turn are attached to vertebra 24 with disc 26 between the two vertebras. As seen in FIG. 8, I-plate 50 is attached to the v-plate 10 with locking screws 62 and 64. Alternatively, I-plate 50 can be attached using a conventional ratchet/cam system, as is well known in the art. I-plate 50 is designed to cover a large portion of the central part of v-plate 10. Locking screw 62 and 64 may be referenced to existing screws and/or sockets on the v-plate 10 or a variable ratchet and cam system can be used to attach I-plate 50 to each v-plate 10. I-plate 50 is designed to cover at least a portion of the screws or other structures used to secure v-plate 10 to prevent screw back out. Once the I-plate 50 is attached to the v-plates 10 the cervical fusion fixation is complete and traditional radiography or fluoroscopy can verify placement and alignment. I-plate 50 may also include one or more optional openings 66 placed such that any surgical grafts can be visualized while I-plate 50 is being applied.

Figure 9A:
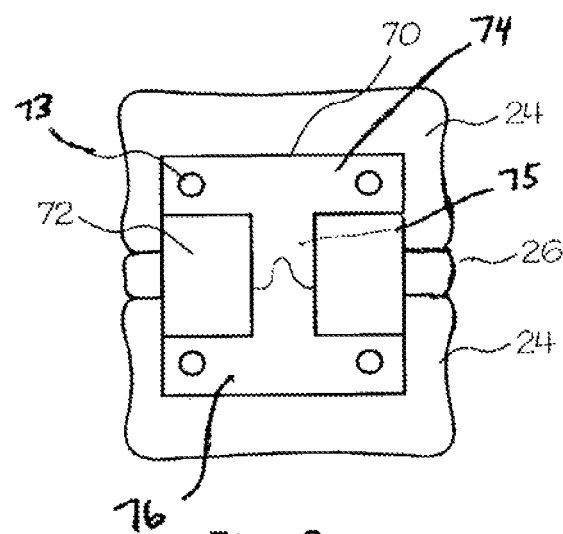
FIG. 9A is a drawing of an elastic I-plate attached to vertebra.
Figure 9B:
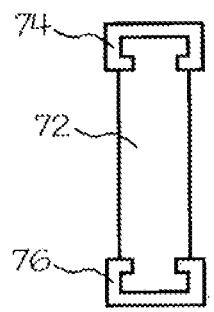
FIG. 9B is a side view of the elastic I-beam.

FIG. 9A is a variable tension plate 70 in accordance with the teachings of the present invention. FIG. 9A illustrates variable tension plate 70 including locking screw 73 and elastic area 72. Variable tension plate 70, as illustrated in FIGS. 9a and 9b, includes a top portion 74 and a bottom portion 76. A connection bar 75, which is a sliding structure comprising groves in one embodiment, connects top portion 74 and bottom portion 76. Part of connection bar 75 is attached to top portion 74 and part to bottom portion 76. Other means for allowing connection bar to expand and contract with the expanding and contraction of variable tension plate 70 can be used. The connection bar 75 limits the contraction of variable tension plate 70 while the elasticity of the elastic area limits the stretching of variable tension plate 70

Elastic area 72 formed from an elastic polymer or other elastic means such as springs to maintain tension between the plates. As the elastic interface is stretched, tension between the plates increases. Elastic means 72 can be designed to either maintain constant tension across the graft interface or to produce a variable tension on the graft depending on how far apart the top portion 74 and bottom portion 76 of variable tension plate 70 are stretched. The elastic polymer or springs means can also be encased within the plate, applied over the plate either laterally or medially, or fixed in some other fashion as would be well known in the art. The advantage of this system is that traditional stresses that exist at a variable angle screw interface in the bone would shift to a bone hardware interface with a variable tension applied over the hardware. The decreased sheer forces at the screw plate in the interface helps to prevent hardware breakage. Additionally the elasticity of the variable tension plate 70 can be used to maintain graft compression over a wide range of tensions and distractions. Alternatively, multi-level variable tension plates 70 could be utilized so that each level of cervical fixations could have its own distraction/tension between two vertebra bodies. FIG. 9B is a side view of the present invention illustrating two parts of the metal I-plates 74 and 76 held together by the elastic area 72. While this represents one possible cross section of elastic plate 70 others would be known to one skilled in the art.

Figure 10:
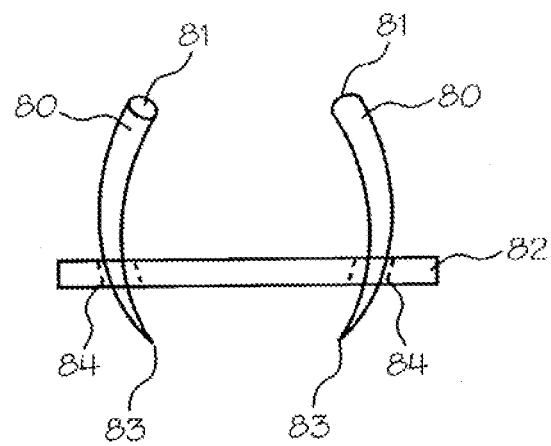
FIG. 10 illustrates a novel attachment system (talon)
Figure 11:
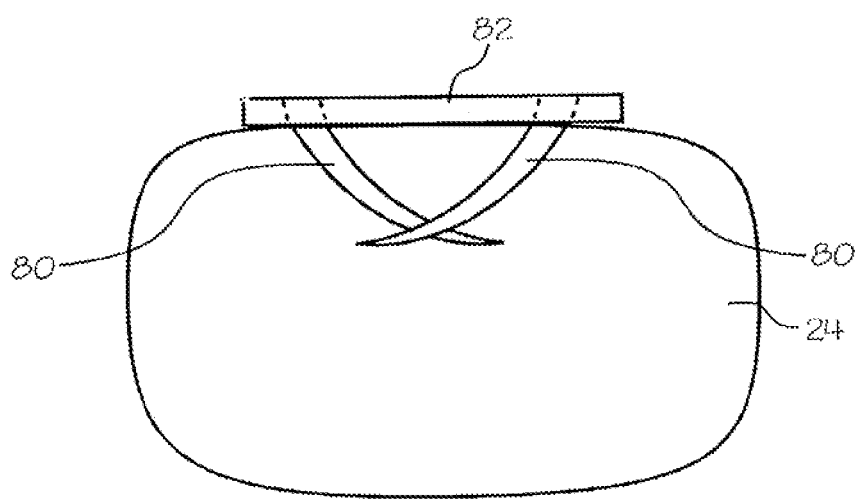
FIG. 11 illustrates the talons as deployed in a vertebra body, securing a cervical plate.

FIG. 10 illustrates a novel attachment system that can be used with v-plate 10 in the present invention. Illustrated are two talons 80 which are inserted through a cervical plate 82 using guide holes 84. Titanium plate 82 may be the v-plate 10. In one embodiment talons 80 are sharp, pointed, curved nails manufactured of titanium that have a decreasing diameter from an end 81 to a tip 83. The tip 83 of the talon 80 is designed to be sharp enough to accelerate into a bone without fracturing the vertebra body. In a typical embodiment talons 80 are applied to either side of a cervical plate 82 into the vertebral body. One talon may have a slight rostral bend and the other a caudal curve. This ensures that each one would move into the body without hitting each other on the way in. Once deployed into the vertebra body the shape of the talons 80 helps to resist pull out force as opposed to traditional screws that resist pull out force solely on the grip between the grooves of the screw and bone mass. The talons 80 may be locked in the place using locking screws or washers or, in present invention, covered by an I-beam 30 or I-plate 50 or variable tension plate 70. In one embodiment the talons 80 may be applied using a modified air gun. In one embodiment, an air gun can be modified to both place the cervical plate 82 and deploy the talons 80 in one operation. By sizing the talon 80 such that they are not long enough to either threaten to impinge on the spinal cord or vertebral arteries, safety is enhanced. In one embodiment, screw threads could be placed into the ends of the talon to facilitate pull out in case the construct has to be removed. FIG. 11 illustrates the talons as deployed in a vertebra body 24, securing a cervical plate 82.

Figure 12:
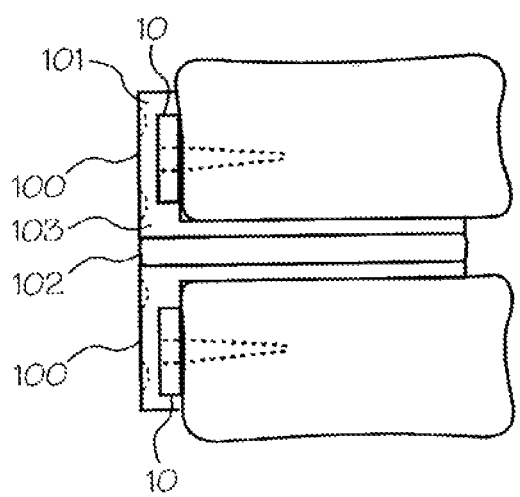
FIG. 12 illustrates an embodiment of the v-plate used in conjunction with an artificial disc.

FIG. 12 illustrates an embodiment of the v-plate 10 used in conjunction with an artificial disc. One problem with current artificial disc is that they require a means to fix the artificial disc to adjacent vertebra and plates and across disc space until the artificial disc is incorporated into the adjacent vertebral level. As illustrated in FIG. 12 this can be accomplished by using the v-plates 10 of the present invention with L-plates 100 mounted over them. In one embodiment the L-plate 100 is a tight angle plate that affixes through the v-plate 10 using a screwing system or a ratchet and cam system. A first leg 101 of the L-plate 100 attaches to the v-plate 10 in the vertebra body face while a second leg 103, at essentially a right angle to first leg 101 and adjacent to the vertebra body, secures to an artificial disc 102. Another L-plate 100 is mounted onto the other vertebra body 24 to also secure the artificial disc. This helps induce fusion of the disc. In this embodiment L-plate 100 can be made from a bio-absorbable material that could include osteogenic or osteoinductive compounds to help induce integration of the L-plate 100 into the vertebra itself. In one embodiment, a complete artificial disc structure comprising two L-plates 100 with an artificial disc mounted between them can be provided. In another embodiment, the artificial disc can be inserted separately between the vertebra and the L-plates inserted in such way that the second leg 103 of the L-plate 100 will attach to the artificial disc. In one embodiment, this can be accomplished using a prong type structure on the second leg of the L-plate 100.

Figure 13:
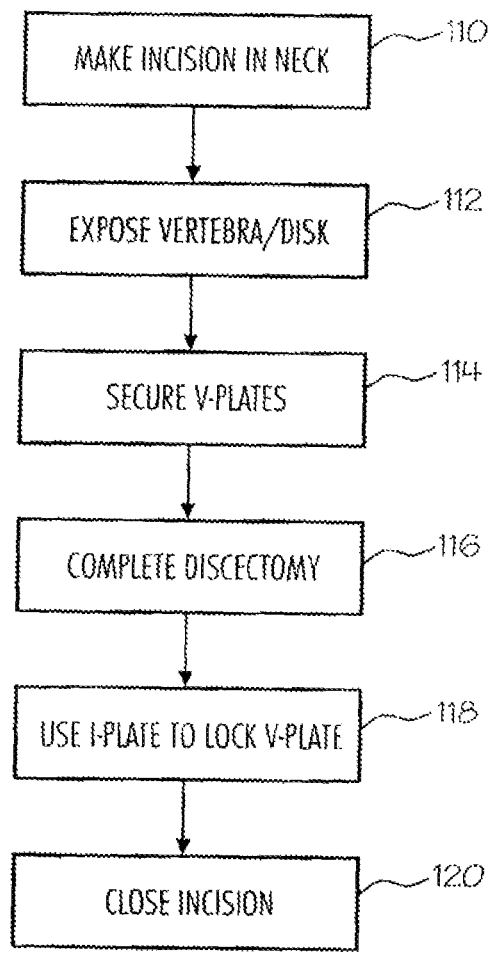
FIG. 13 is a flow chart illustrating a method of using the modular plating system in an anterior cervical discectomy.

FIG. 13 is a flow chart illustrating a method of using the modular plating system in an anterior cervical discectomy. In a first step 110 a small incision is made in the front of the neck, to one side. Next, in step 112, fat and muscle are pulled aside with a retractor, the disc is exposed between the vertebras. In a next step 114, the v-plates 10 are secured to the vertebral bodies of each level to be fixated. This is different than current methods employing vertebra plates that are not secured until the end of the operation. Next, in step 116, the discectomy is completed. Part of the disc is removed and specialized instruments or a surgical drill may be used to enlarge the disc space. This will help the surgeon to empty the disc space fully and relieve any pressure on the nerve or spinal cord from bone spurs or the ruptured disc. If a bone graft is used, it is placed in the disc space to help fuse the vertebrae it lies between. Any of several graft shapes may be used. After the graft is in place, cervical alignment is optimized and adequate compression is applied. During the operation, retractors can be attached to the v-plate to hold body structure such as the esophagus. Then, in step 118, the I-plate (or I-beam 30, variable tension plate 70 or similar structure) is locked to the v-plates 10 at each level. If necessary, traditional radiography or fluoroscopy can be used to verify hardware placement and cervical alignment. In step 120, the neck incision is closed in several layers. Unless dissolving suture material is used, the skin sutures (stitches) or staples will have to be removed after the incision has healed.

Having now described preferred embodiments of the invention modifications and variations may occur to those skilled in the art. The invention is thus not limited to the preferred embodiments, but is instead set forth in the following clauses and legal equivalents thereof. For example, although the discussions only disclosed the use of the present invention for attaching of two vertebras together, multiple vertebras can be connected without departing from the scope of the present invention.

What is claimed:

1. A modular system for anterior fixation of a first and second vertebrae comprising:
   a plurality of fasteners, the plurality of fasteners having a fastener radius of curvature;
   a first v-plate comprising a connection interface, the first v-plate have a plurality of fastener holes, each of the plurality of fastener holes adapted to receive one of the plurality of fasteners such that the first v-plate is operable to be attached to a first vertebra;
   a second v-plate comprising a connection interface, the second v-plate having a plurality of fastener holes, each of the plurality of fastener holes adapted to receive one of the plurality of fasteners such that the second v-plate is operable to be attached to a second vertebra; and
   an I-plate comprising an I-beam configuration adapted to couple the I-plate to the connection interface of the first v-plate along a central part of the first v-plate and the connection interface of the second v-plate along a central part of the second v-plate, the I-plate having a plurality of indentations along opposing lateral edges, the plurality of indentations comprising a plate radius of curvature greater than the fastener radius of curvature to allow for adjustment between the I-plate and the first v-plate and the second v-plate, the I-plate operable to abut the plurality of fasteners along the opposing lateral edges at the plurality of indentations so as to prevent back out of the structures.

2. The system of claim 1 wherein the I-plate comprises a single piece structure operable to span from the first v-plate to the second v-plate.

3. The system of claim 2 wherein the I-plate includes one or more openings through the I-plate to allow for visual access to the area below the I-plate once the I-plate is installed.

4. The system of claim 1 further comprising a retractor adapted to be attached to the first v-plate and the second v-plate.

5. The system of claim 4 further comprising a ratcheting system adapted to be attached to the retractor to allow for manual separation or contraction of the first vertebra and the second vertebra.

6. The system of claim 1 further comprising one or more additional v-plates adapted to be attached to one or more vertebra, one or more I-plates adapted to attach adjacent ones of the one or more additional v-plates, the first v-plate, and the second v-plate.

7. The system of claim 1, wherein the first v-plate and second v-plate are adapted to be attached to the first vertebra and the second vertebra using a curved talon, the talons having a pointed end that inserts into the bone and a second end that secures the first v-plate and second v-plate to the first vertebra and the second vertebra.

8. The system of claim 1, wherein the system is adapted for use in anterior cervical spine operations.

9. The system of claim 1 wherein the I-plate includes a plurality of indentations formed along each side, the plurality of indentations having a radius of curvature greater than the head of a fastening device used to affix the I-plate to the first v-plate and the second v-plate, the indentations allowing for adjustment of the I-plate as it attaches to the first v-plate and second v-plate.

10. The system of claim 1 wherein the first v-plate is adapted to be attached to the first vertebra by one or more screws and the second v-plate is adapted to be attached to the second vertebra by one or more screws.

11. The system of claim 10 wherein the I-plate lateral edges engage at least part of the one or more screws used to attach the first v-plate and the one or more screws used to attach the second v-plate.

* * * * *

UNITED STATES PATENT AND TRADEMARK OFFICE
CERTIFICATE OF CORRECTION

| | | |
|---|---|---|
| PATENT NO. | : 8,518,041 B2 | Page 1 of 1 |
| APPLICATION NO. | : 12/766728 | |
| DATED | : August 27, 2013 | |
| INVENTOR(S) | : Lemole, Jr. | |

It is certified that error appears in the above-identified patent and that said Letters Patent is hereby corrected as shown below:

On the title page, in Item [54] and in the specification, column 1, line 1, in "Title", delete "MODULUS PLATING SYSTEM" and insert -- MODULUS PLATING SYSTEM AND METHOD --, therefor.

On the title page, in Item [75], in column 1, in "Inventor", line 1, delete "Michael G. Lemole, Jr.," and insert -- G. Michael Lemole, Jr., --, therefor.

Signed and Sealed this
Third Day of June, 2014

Michelle K. Lee
*Deputy Director of the United States Patent and Trademark Office*